United States Patent [19]

van Andel

[11] Patent Number: Plant 5,529

[45] Date of Patent: Aug. 6, 1985

[54] CARNATION NAMED STANARTHUR

[75] Inventor: Jacob van Andel, Aalsmeer, Netherlands

[73] Assignee: B. V. Handelskwekerij/M. C. van Staaveren, Aalsmeer, Netherlands

[21] Appl. No.: 556,613

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Chas. W. Rummler

[57] ABSTRACT

A new carnation variety having blooms of medium size and abundant petalage which is generally of an almost white color and is marked near its outer end by dark red stripes of various lengths which gives the fully opened bloom a startling and very unusual overall variegated cream and red coloration, the plant itself having an upright growth habit with good strength and an abundant production of foliage.

1 Drawing Figure

BACKGROUND OF THE NEW PLANT

This new variety of carnation was discovered by me in 1976 as a sport of the variety "Londorga" being grown in greenhouse, for commercial purposes, at Aalsmeer, The Netherlands. This new plant was discovered by me in 1976 and its unusual coloration prompted me to propagate the plant by means of cuttings, which I did at Aalsmeer where I carried on such propagation through several successive generations and over a period of years and thereby found that the distinctive and novel characteristics of this new variety would hold true from generation to generation and appeared to be firmly fixed.

DESCRIPTION OF THE DRAWING

My new carnation variety is illustrated by the accompanying photographic drawing which shows the nature of the blooms in full color, the principal figure being a three-quarter view of a mature bloom and the other views being partial face views of companion flowers, all of which illustrate the general characteristics of the blooms of this variety, the colors shown being as nearly true as it is reasonably possible to obtain by conventional photographic procedures.

DESCRIPTION OF THE NEW PLANT

The following is a detailed description of my new carnation plant based upon observation of greenhouse plants made at Aalsmeer, The Netherlands, in the summer of 1983, the color designations being according to The R.H.S. Colour Chart published by The Royal Horticultural Society of London, England.

THE PLANT

Origin: Sport.
Parentage: The carnation "Londorga".
Classification:
- *Botanic.*—*Dianthus caryophyllus* Hybrid.
- *Commercial.*—Greenhouse carnation.

Form: A tall bush.
Height: Normal.
Growth habit: Sturdy and upright with good strength and normal branching character.
Foliage:
- *Quantity.*—Abundant.

- *Number of leaves.*—Vary according to season.
- *Size of leaf.*—Average.
- *Shape.*—Oblong.
- *Texture.*—Smooth.
- *Color.*—Both upper side and under side — Blue/-Green with waxy layer.

THE BUD

Size: Medium.
- *Diameter.*—About 1.5 cm.
- *Length.*—About 3 cm.

Form: Generally cylindrical with pointed apex.
Rate of opening: Normal.
Sepals: Of normal shape and number and the sepals curl back when the flowers open.
- *Color.*—Inside — Grey/Green. Outside — Grey/-Green.

Calyx:
- *Shape.*—Funnel-shaped.
- *Size.*—Medium.
- *Aspect.*—Smooth.
- *Splitting.*—The calyx rarely splits.

Flower stem:
- *Length.*—Average.
- *Character.*—Strong and erect.
- *Color.*—Dark Green.

THE FLOWER

Blooming habit: Continuous.
Size of bloom: Medium.
- *Diameter.*—About 8 cm.
- *Depth.*—About 4 cm.

Borne: Singly.
Shape:
- *When bloom first opens and as it matures.*—High centered.

Petalage:
- *Number of petals.*—From 50 to about 60.
- *Arrangement.*—Loosely imbricated.
- *Form.*—Fan-shaped with serrated to almost dentated margin.
- *Texture.*—Soft.
- *Appearance.*—Shiny.
- *Color.*—All petals: Upper side — Body — R.H.S. 157C. Base — Pale Green. Reverse side — R.H.S. 157C. Marginal stripes — Red. The colors are the same for all seasons.

Flower stem:
*Length.*—Varies according to season.
*Character.*—Strong and upright.
*Color.*—Dark Green.
Fragrance: Slight.
Persistence: The petals hang on and dry.
Lasting quality:
*On plant.*—About 20 days.
*As cut flower.*—From 10 to about 15 days.

REPRODUCTIVE ORGANS

Stamens: Of average number and arrangement.
*Anthers.*—Size: Medium. Color: Cream.
*Pollen.*—There is no pollen.
Pistils:
*Number.*—One.

*Style.*—Length: Approximately 27 mm. Color: White/Cream.

This carnation most nearly resembles its parent "Londorga" (unpatented) in substantially all of its physiological characteristics except the color of its blooms and the fact that the new variety is less susceptible to *Fusarium oxysporum.*

I claim:

1. The new and distinct carnation variety, substantially as herein shown and described, characterized by its continuous production of medium sized blooms of almost white color variegated by longitudinal stripes appearing at the outer ends of most of its petals and its apparent resistance to *Fusarium oxysporum.*

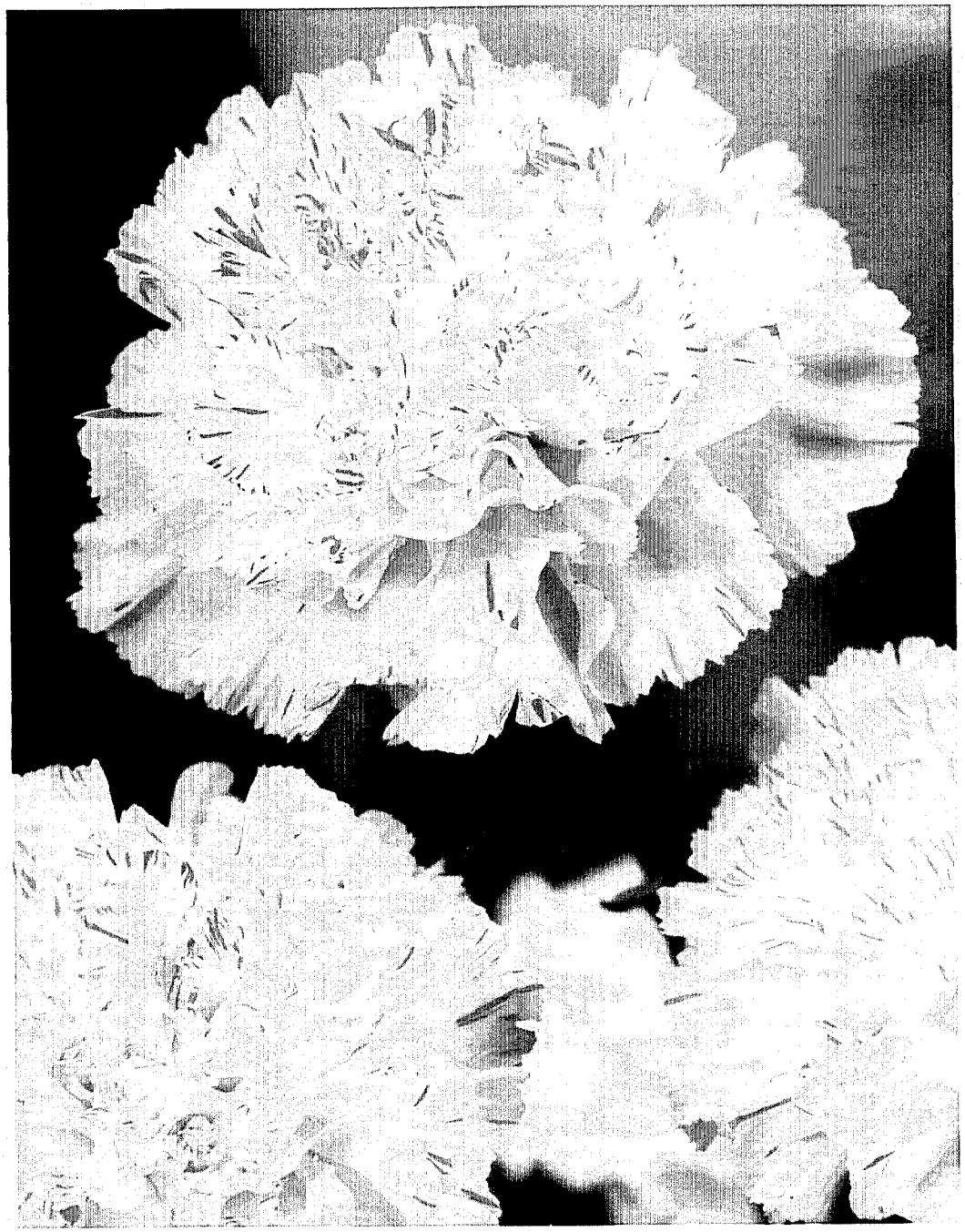

* * * * *